(12) United States Patent　　(10) Patent No.: US 7,762,262 B1
Granja　　(45) Date of Patent: Jul. 27, 2010

(54) DISPOSABLE PROPHYLACTIC GARMENT FOR RESTRICTING SEXUALLY TRANSMITTED DISEASES FOR MEN

(76) Inventor: Jorge L. Granja, 7972 Ranchito Ave., Panorama City, CA (US) 91402

( * ) Notice: Subject to any disclaimer, the term of this patent is extended or adjusted under 35 U.S.C. 154(b) by 206 days.

(21) Appl. No.: 12/008,664

(22) Filed: Jan. 14, 2008

(51) Int. Cl.
*A61F 6/02* (2006.01)
*A61F 6/04* (2006.01)
*A61F 5/44* (2006.01)
*A41B 9/08* (2006.01)
*A41B 9/00* (2006.01)
*A41B 9/14* (2006.01)

(52) U.S. Cl. .............. 128/844; 128/842; 128/917; 128/918; 2/71; 2/73; 2/76; 2/400; 2/401; 2/402; 2/403; 604/347; 604/349; 604/353

(58) Field of Classification Search .......... 128/842, 128/844, 917, 918; 2/21, 71, 73, 76, 236–237, 2/400–403; 604/347–353
See application file for complete search history.

(56) References Cited

U.S. PATENT DOCUMENTS

| | | | |
|---|---|---|---|
| 2,128,876 A * | 8/1938 | Boysen | 2/237 |
| 4,807,611 A | 2/1989 | Johnson | |
| 4,843,654 A * | 7/1989 | March | 2/227 |
| 4,942,885 A | 7/1990 | Davis et al. | |
| 4,981,147 A | 1/1991 | Barnett | |
| 5,156,165 A | 10/1992 | Wu | |
| 5,513,653 A | 5/1996 | Huang | |
| D419,233 S | 1/2000 | Brodie | |
| 2003/0150463 A1 * | 8/2003 | Anderson | 128/842 |

* cited by examiner

*Primary Examiner*—Patricia M Bianco
*Assistant Examiner*—Brandon Jackson
(74) *Attorney, Agent, or Firm*—Ashkan Najafi

(57) ABSTRACT

A garment includes a bifurcated body having front and rear sections wherein the front section is provided with a sheath oriented about a genital region and includes a ribbed outer surface. The rear section is provided with a plurality of apertures and is oriented about a buttock region respectively. The ribbed outer surface includes a plurality of protrusions. The apparatus further includes a mechanism for fastening the garment about the user's waist. A condom is positionable about a user's penis wherein a proximal end portion of the condom is engageable about the ribbed outer surface of the sheath, defining a frictional contact area for assisting to maintain the condom positioned about the penis during sexual activities.

6 Claims, 5 Drawing Sheets

DISPOSABLE PROPHYLACTIC GARMENT FOR RESTRICTING SEXUALLY TRANSMITTED DISEASES FOR MEN

CROSS REFERENCE TO RELATED APPLICATIONS

This application claims the benefit of U.S. patent application Ser. No. 11/049,779, filed Feb. 4, 2005.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to the field of disease prevention, and more particularly, to devices designed to prevent the spread of sexually transmitted diseases.

2. Prior Art

The last decade has seen a remarkable rise both in the incidence of STD's and the impact of such diseases on the public consciousness. Penicillin and its progeny had relegated "traditional" STD's, such as gonorrhea, to a matter of little public concern by the end of the 1960's. That situation changed drastically, however, with the advent of herpes. A viral infection that proved resistant to all known forms of treatment, herpes presented a serious threat to persons who participated in frequent sexual activity with a number of partners. The impact of herpes, however, proved almost minuscule when the Acquired Immune Deficiency Syndrome (AIDS) epidemic surfaced in the 1980's.

Failing a massive change in behavior patterns, many see the condom as the only real solution to the containment of AIDS. Several serious drawbacks to that solution, however, limit the success of this method of prevention. First, a particular condom may not fulfill its function, either because it does not remain in position, or it breaks during use, or it may remain in position but serve as a sheath for infectious biological products to travel onto the perineum. This problem is particularly acute in ano-genital intercourse, due to the general lack of clearance between the orifice and the penis. The danger of relying upon the condom in such situations is exacerbated, of course, by the fact that this activity perhaps poses the greatest danger of infection.

Moreover, spillage of semen from a condom is a common occurrence, and leakage is practically guaranteed, especially when the wearer is supine. The condom is neither designed nor commonly used for the purpose of preventing contact between semen and the perineum of either or both partners, and thus it is not surprising that it does not serve that purpose. The risk presented by such contact, however, makes the condom a limited tool for preventing the spread of AIDS.

In addition to such possible transmission of the AIDS virus by entry through localized skin defects in the recipient, there is also the possibility that other sexually transmitted diseases (STDs) may be similarly transmitted, including clamydia, herpes, papilloma, syphilis, gonorrhea, lymphogranoloma venerum, and the like. The foregoing has heightened pertinence in view of the fact that localized skin disorders occur with high frequency in the lower abdominal and thigh regions. Examples include infected ingrown pubic hairs, pimples, blackheads, boils, rashes, herpes, dermatitis, allergic reactions, and the like, which, comprise or result in localized skin discontinuities and other defects in skin integrity. Conventional prophylactic devices do not cover the abdominal skin areas, allowing for transmission of such diseases, regardless of the use of these devices.

Accordingly, a need remains for a disposable prophylactic garment for restricting transmittal of body fluids in order to overcome the above-noted shortcomings. The present invention satisfies such a need by providing a prophylactic garment that is practical in design, increases safe intercourse, and is effective in use. Such a garment covers a larger area of the abdominal area, preventing skin contact. The garment is offered in a variety of sizes and styles to fit the needs and preferences of all individuals. The garment further advantageously decreases the possibility of the prophylactic device slipping off during intercourse and is durable in construction, preventing the tearing thereof.

BRIEF SUMMARY OF THE INVENTION

In view of the foregoing background, it is therefore an object of the present invention to provide a disposable prophylactic garment for use by men during sexual intercourse. The garment protects the wearer from body fluids and sexually transmitted diseases. The garment features a unique design offering a disposable boxer styled garment for men that offers protection to the genitals during sexual encounters. The garment covers external genitalia, including the scrotum, anus, inner thighs and abdomen. An open sheath at the front of the garment encases the lower shaft of the penis, leaving the head and a portion of the shaft exposed, and is designed for those wishing to enjoy contact with their partners. A conventional condom is used with this device for full protection. The integrally formed sheath at the front of the garment has incorporated raised protrusions designed to make the surface of the sheath non-slippery, making the condom less likely to slip off during intercourse. These raised protrusions on the sheath act as a condom holder and also add stimulation to the sexual act.

When the condom is used, it is positioned over the head of the penis and down over the partial ribbed sheath integrally formed within this device. The ribbed outer surface of the sheath includes a plurality of protrusions. Such protrusions may be of any size, shape form or quantity. This garment features a curved inseam at the legs for greater freedom of movement and seams at the hips with a slit for greater leg room for maximum comfort. The garment may have an elastic waistband at the back for proper fit, depending upon the elasticity of the material used to construct the device.

The garment further includes a bifurcated body formed from pliable and fluid impermeable material including front and rear sections. The device provides men with improved safety through increased protection to the entire genitalia area. The garment covers the front and back of the wearer, as well as the inner thighs. The device covers the genitalia, including a portion of the lower abdomen, the penis, the scrotum and anal area.

When the device is used with a condom, the condom is less likely to slip off during or after intercourse. This increases the overall effectiveness of such an aid. In addition, a greater portion of the penis is protected against any sexually transmitted diseases spread through contact. The garment also shields the male genitals from moisture during sexual intercourse. This device accommodates a condom for those wishing to prevent pregnancy or additional contact. The condom, when used, is less likely to slip off during intercourse, offering greater protection against pregnancy. Conventional condoms provide protection to a limited area of the genitals, leaving large areas exposed to contact.

The garment offers convenience and practicality. By providing greater protection to the entire genital area, the user would be less likely to contract sexually transmitted diseases known to spread through contact. Contact with body fluids and other irritants are also reduced.

The appealing features of this garment are practical design, added safety, and greater effectiveness, as well as its ability to protect the user and his partner from the potential spread of contact related diseases. This device could be produced easily using conventional and readily available materials and manufacturing processes. No new production technology would be required. The garment may be produced from any waterproof material such as polyurethane or any other soft, flexible, impermeable and expandable material. The disposable garment would be offered in various sizes and designs. Upon use, the garment would be appropriately discarded.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

Figure 1:
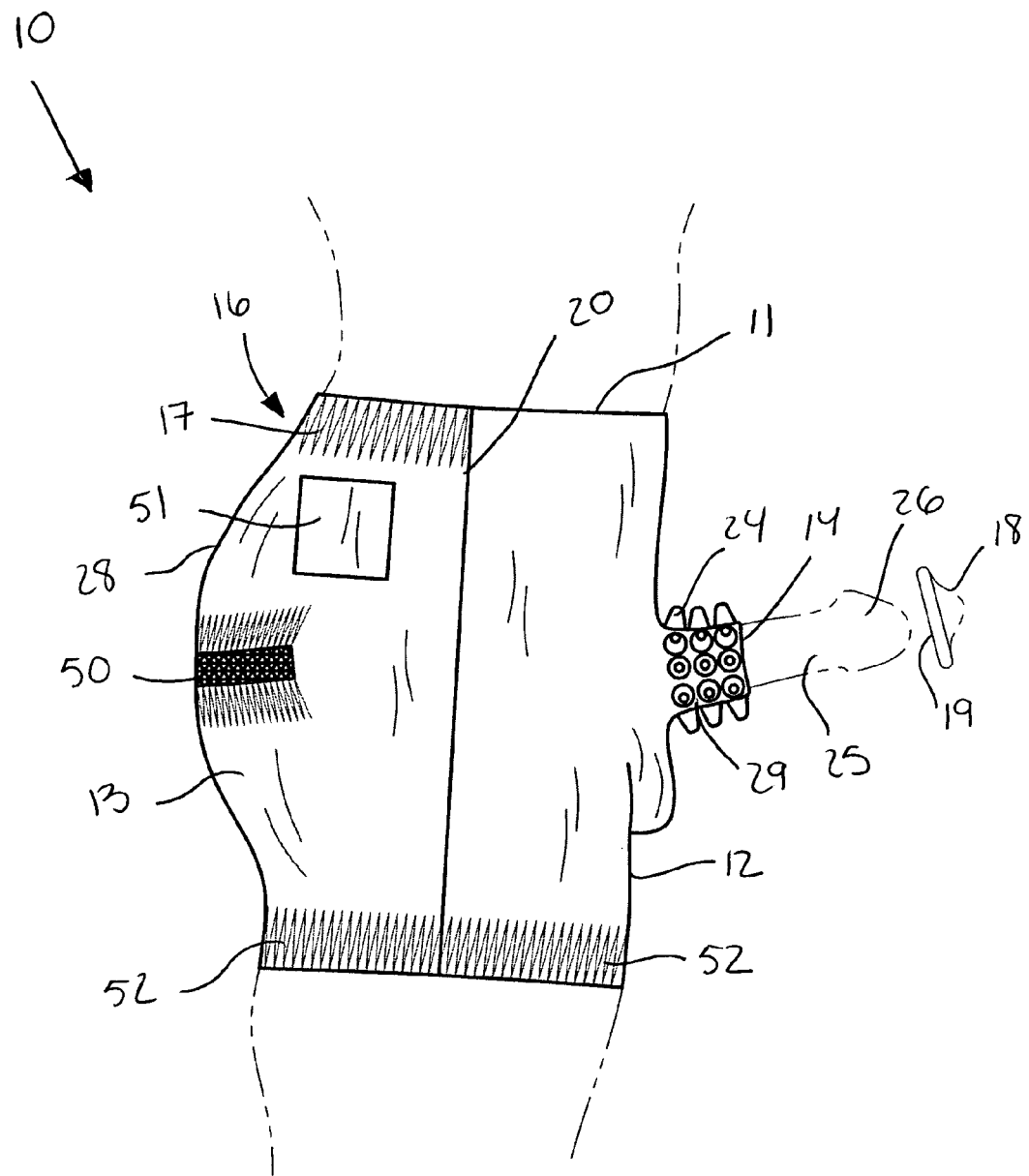
FIG. 1 is a side-elevational view showing a disposable prophylactic garment for restricting transmittal of sexually transmitted diseases in a preferred environment, in accordance with the present invention.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The apparatus of this invention is referred to generally in FIGS. 1-5 by the reference numeral 10 and is intended to provide a disposable prophylactic garment for restricting transmittal of sexually transmitted diseases during sexual intercourse. It should be understood that the apparatus 10 may be used to provide protection in many different types of activities and should not be limited to only sexual intercourse activities.

The apparatus relates to a prophylactic garment and, more particularly, to a prophylactic garment for restricting the transmittal of bodily fluids and skin to skin sexually transmitted diseases such as possible transmission of the AIDS virus by entry through localized skin defects in the recipient, there is also the possibility that other sexually transmitted diseases (STD's) may be similarly transmitted, including clamydia, herpes, papiloma, syphilis, gonorrhea, lymphogranoloma venerum, and the like. The foregoing has heightened pertinence in view of the fact that localized skin disorders occur with high frequency in the lower abdominal and thigh regions.

Examples include infected ingrown pubic hairs, pimples, blackheads, boils, rashes, herpes, dermatitis, allergic reactions, and the like, which often result in localized discontinuities and other defects in skin integrity. Conventional prophylactic devices do not cover the abdominal and genital skin areas, allowing for transmission of such diseases. The garment 10 features a unique design offering a disposable boxer-styled garment 11 for men that offers protection to the genitals during sexual encounters. The garment 10 covers the external genitalia, including the scrotum, anus, inner thighs and abdomen.

Referring initially to FIG. 1, the apparatus 10 includes a bifurcated body 11 formed from a soft, flexible, impermeable and expandable material such as Vinyl, Latex, Polyurethane or any other soft flexible impermeable and expandable material, including integrally disposed front 12 and rear 13 sections. Such a body 11 has a centrally disposed longitudinal axis and is removably positionable about a user's waist wherein the front section 12 is oriented about a genital region and the rear section 13 is oriented about a buttock region respectively. The body 11 advantageously covers a much larger area of the groin region than a conventional condom, thus protecting each participant from bodily fluids and other diseases that may be transmitted via skin contact.

Figure 2:
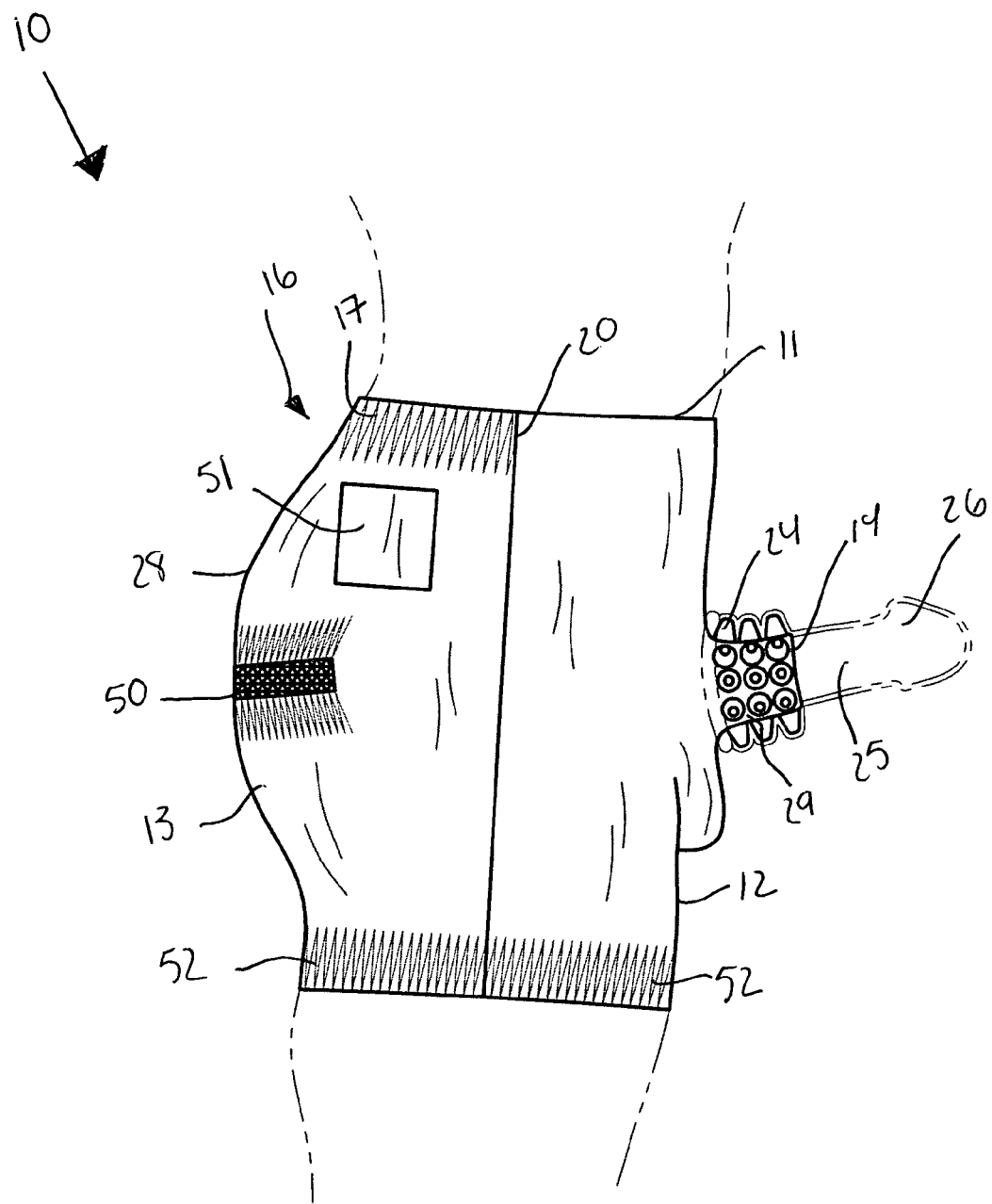
FIG. 2 is a side-elevational view showing a disposable prophylactic garment, with a condom in place, in accordance with the present invention.

Referring to FIGS. 1 and 2, the front section 12 is provided with an open sheath 14 sized and shaped for receiving a human penis 25 therethrough. Such a sheath 14 has a substantially annular shape and is integral with the front section 12. The sheath 14 further includes a ribbed outer surface 29 for holding the condom 18 and advantageously enhancing sexual pleasure during love-making activities. The sheath 14 is disposed centrally of the front section 12 and is forwardly extendable along selected arcuate paths for assisting a user to maneuver the penis 25 as desired. The ribbed outer surface 14 is a feature that further increases the appeal of the apparatus 10, advantageously increasing the likelihood of the same being used, to the advantage of both individuals, during love making activities.

Figure 4:
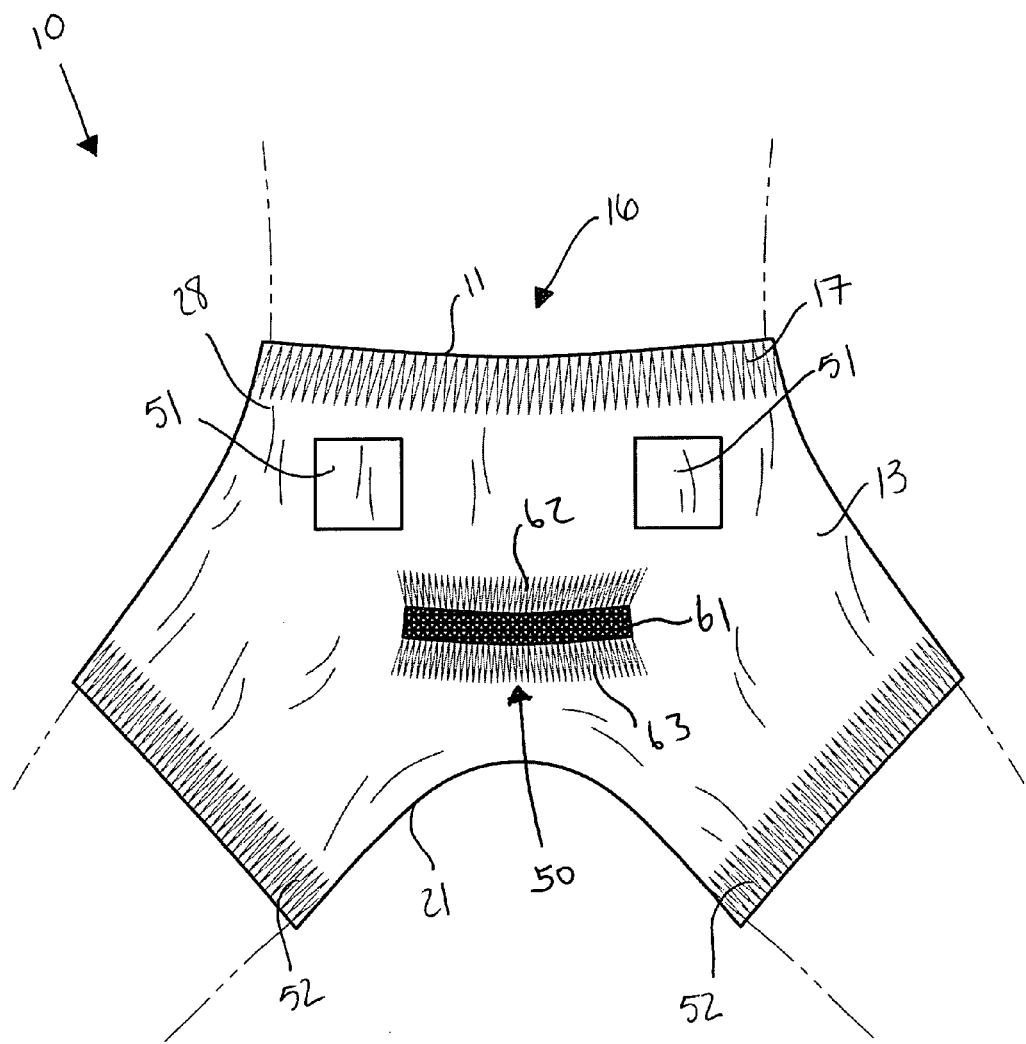
FIG. 4 is a rear elevational view of the apparatus shown in FIG. 1.

Referring to FIG. 4, the open sheath 14 at the front 11 of the garment 10 encases the lower shaft of the penis 25, leaving the head and a portion of the shaft exposed which is designed for those wishing to enjoy contact with their partners. A conventional condom is to be used in conjunction with the device 10 for full protection.

Referring to FIG. 2, the garment 10 features seams at the hip 20, using the simplistic process of heat sealed seams, making this a practical manufacturing process. Any other means available to achieve manufacture of these specifications may be used. The disposable garment 10 is to be offered in various sizes and designs.

Referring to FIG. 4, the ribbed outer surface 29 includes a plurality of protrusions 24. Such a ribbed outer surface 29 is disposed adjacent a base of the penis 25 so that a distal end 26 of the penis 25 can advantageously become exposed for pleasure.

Figure 3:
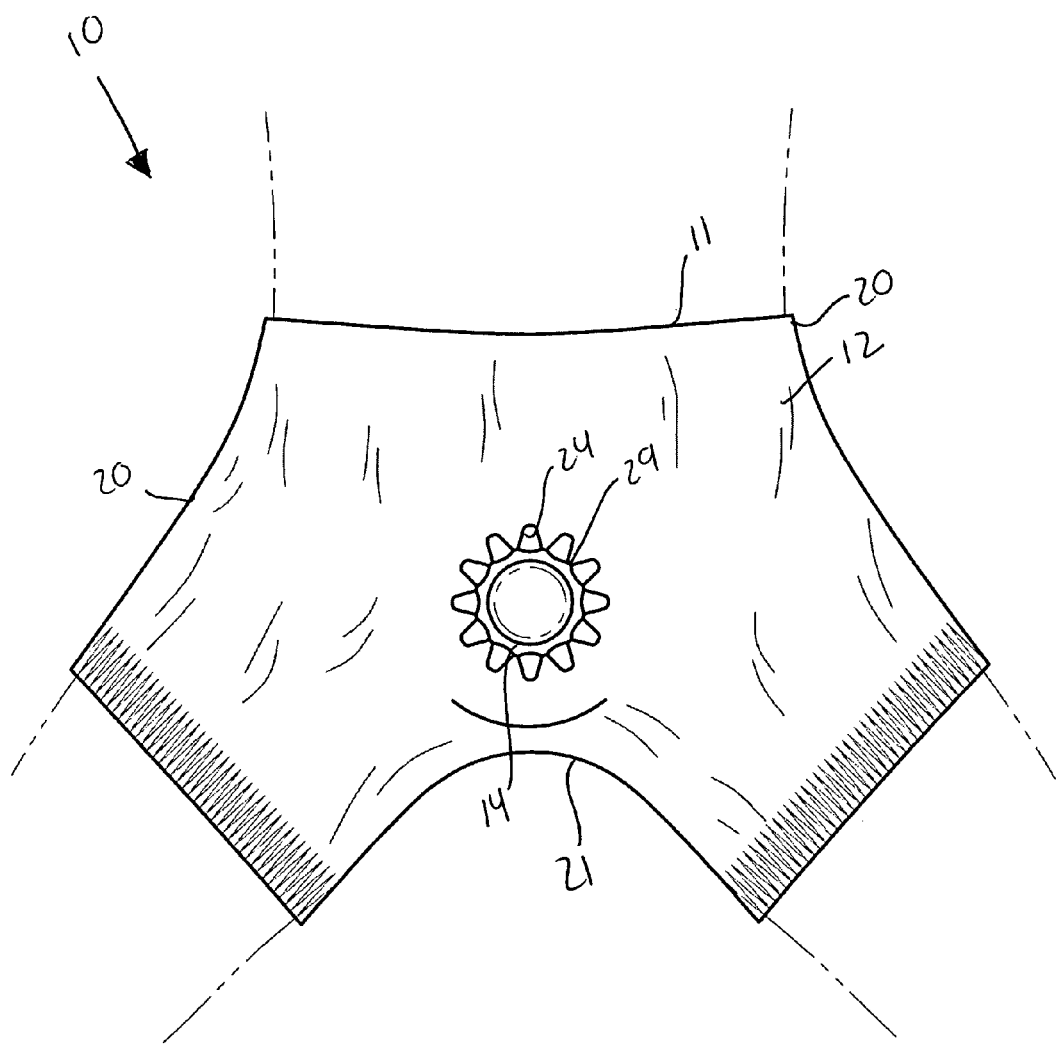
FIG. 3 is a front elevational view of the apparatus shown in FIG. 1.

Referring to FIGS. 1 and 3, the apparatus 10 further includes a mechanism 16 for fastening the apparatus 10 about the user's waist so that the apparatus 10 can advantageously be maintained at a substantially stable position during the activities. This feature advantageously allows individuals of varying waist sizes to use the apparatus 10, limiting the number of sizes that must be produced and resulting in production savings that can then be passed on to the consumer in the form of an affordable price. In particular, mechanism 16 includes a gathered portion 28 integrally attached to the rear section 13 adjacent the straps 17 for cooperating therewith and for providing resilient tension about the user's waist, further ensuring that the apparatus 10 remains in position during the use thereof. Such a gathered portion 28 may include a conventional elastic strap or band commonly employed by undergarments, well known in the industry. Of course, a draw string or other non-elastic ties may be used by the present invention without departing from the true scope.

Referring to FIG. 4, a condom 18 is positionable about the penis wherein a proximal end portion 19 of the condom 18 is engageable about the ribbed outer surface 29 of the sheath 24. Such a ribbed outer surface 29 defines a frictional contact area for advantageously assisting to maintain the condom 18 positioned about the penis during the activities. A problem with conventional wearing of condoms 18 is their propensity to slip off of the penis during love making activities, leading to the unwanted exposure of an individual's partner to his bodily fluids. Thus, the above mentioned feature increases the safety characteristics of the apparatus 10.

Figure 5:
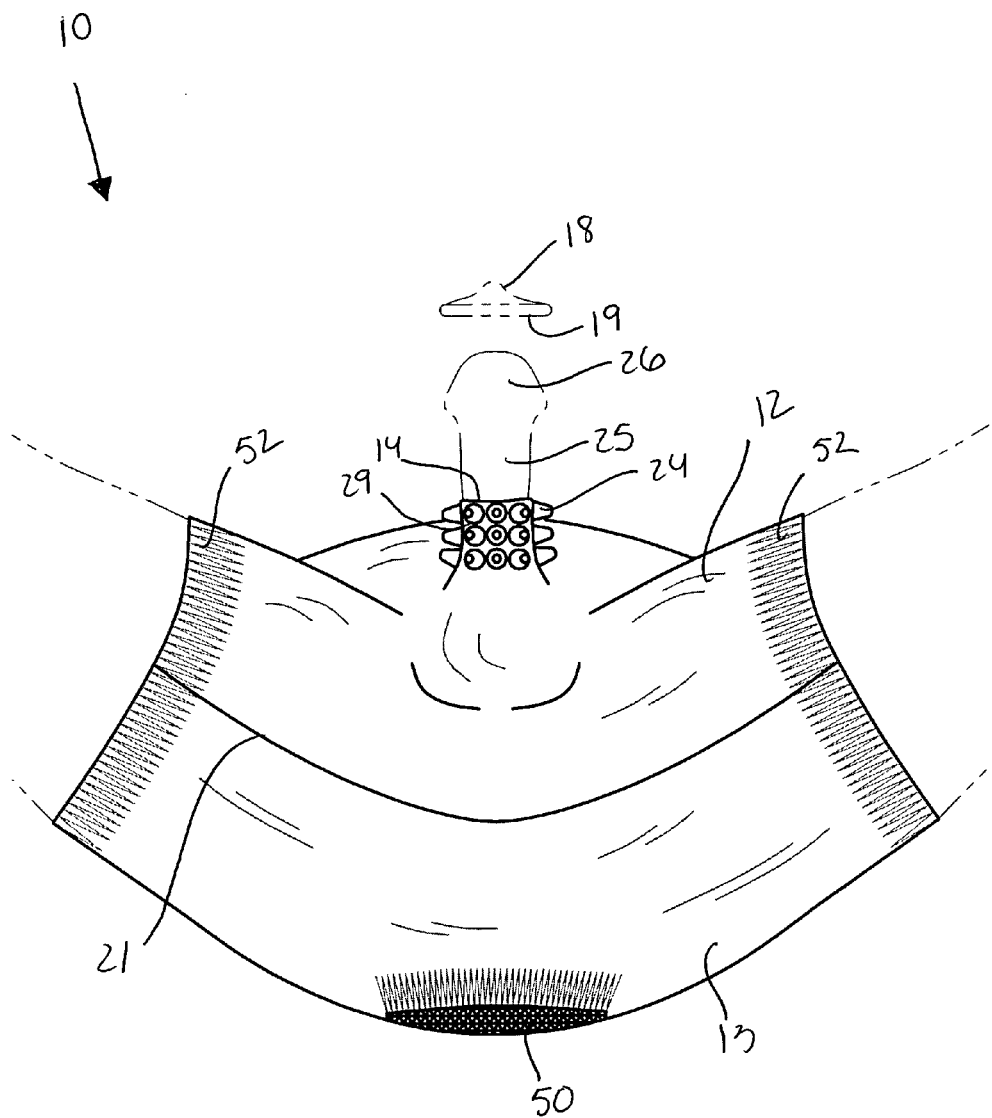
FIG. 5 is a bottom planar view of the apparatus shown in FIG. 1.

Referring to FIG. 4, in operation, the condom 18 is to be positioned over the head and shaft of the penis 25 and down over the partial ribbed sheath 14 integrally formed as shown in FIGS. 4 and 5. The ribbed outer surface 16 of the sheath includes a plurality of protrusions 24. Such protrusions 24 may be of any size, shape, form or quantity. The garment 10 may have an elastic waistband 17 at the back 13 for proper fit, depending upon the elasticity of the material used to construct the device 10.

Referring back to FIG. 1, the garment 10 covers the genitalia, including a portion of the lower abdomen, penis 25, the scrotum and anal areas also are covered. When the condom 18 is used, it is less likely to slip off during or after intercourse. This would increase the overall effectiveness of such an aid. In addition, a greater portion of the area would be protected against any sexually transmitted diseases spread through contact. The garment 10 shields the male genitals from moisture and skin contact during sexual intercourse. The device 10 also accommodates a condom 18 for those wishing to prevent pregnancy or additional contact. The condom 18, if used, is less likely to slip off during intercourse, offering greater protection against pregnancy. Conventional condoms provide protection to a limited area of the genitals, leaving large areas exposed to contact.

An additional gathered portion 50 is attached to the rear section 13 of the garment 10 and provides resilient tension about the buttock region of the user. The garment 10 can thereby be advantageously maintained at a substantially stable position during repeated sexual activities. Such an additional gathered portion 50 spans along a partial width of the rear section 13 and is centered between left and right sides of the garment 10. In particular, the additional gathered portion 50 has a heavily concentrated resilient central elastic section 61 that is substantially rectangular and spans substantially parallel to a waist of the user, as perhaps best shown in FIG. 4.

Surrounding top and bottom longitudinal sides of the central elastic section 61 are less concentrated resilient elastic sections 62, 63 that extend along the entire longitudinal lengths of the longitudinal sides of the central elastic section 61, respectively. Advantageously, such a structural arrangement of heavy and less concentrations of resilient elastic sections provides an unexpected benefit by solving the problem of undesirable vertically shifting of the garment 10 along the rear section 13 while the user is thrusting along a repeated and oscillating direction during intercourse. Accordingly, the problem of premature shifting of the rear section of the garment 10 is solved while the front section 12 of the garment is allowed to shift to alleviate pressure on the scrotum and penis shaft during the trusting activities.

Referring to FIG. 5, it can be appreciated that the garment is allowed to resiliently stretch side-to-side along a direction that is defined orthogonal to a trusting motion during intercourse so that uncomfortable tension is eliminated along the penis shaft and about the scrotum. The waist line defining the top edge of the front section 12 does not have any elastic bands so that regions surrounding the penis shaft and scrotum are freely adaptable and shifted during thrusting activities while the rear section 13 is adequately engaged about the user buttock.

The garment may further require lubricant to make it easier to insert the penis into the condom 18. Lubricant is provided with the garment 10 along with a plurality of condoms 18. The garment features pocket 52 for housing the lubricant and the condom 18. In addition, the rear section 13 has an elastic strap 50 to add tension to the front section 12. The legs of the garment include two elastic bands 52 to keep a user from being exposed to sexual fluids. Each elastic band extends along an entire perimeter of the front and rear sections 12, 13 to form a continuous elastic perimeter around an entire leg portion formed at left and right bottom sides of the garment 10.

A method for reducing a risk of is exposed to sexually transmitted diseases includes the steps of: providing a bifurcated body formed from pliable and fluid-impermeable material and including integrally disposed front and rear sections; removably positioning the body about a user's waist wherein the front section is oriented about a genital region and the rear section is oriented about a buttock region respectively; positioning a male penis through a sheath formed in the front section such that a ribbed outer surface is disposed at a base of the male penis; fastening the garment about the user's waist so that the garment can be maintained at a substantially stable position during the activities; positioning a condom the male penis wherein a proximal end portion of the condom is engaged about the ribbed outer surface of the sheath; and creating a frictional contact area between the condom and the ribbed outer surface for maintaining the condom positioned about the penis during the activities.

The method further includes the steps of: providing a resiliently gathered elastic portion integrally attached to the rear section and formed from elastic material for providing resilient tension about the user's waist; providing an additional gathered elastic portion attached to the rear section and providing resilient tension about a buttock region; allowing the front section of the garment to freely slide along a front side of the user during thrusting motions while the rear section of the garment remains resiliently engaged with the user waist; attaching a plurality of pockets to the rear section of the garment; and removably positioning lubrication and the condom into the pockets respectively.

The appealing features of the apparatus 10 are its practical design, added safety, and ability to protect a user and his partner from sexually transmitted diseases. By providing protection to the entire genital area, contact with body fluids and other irritants is reduced, decreasing the chances of being infected.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A male garment for reducing the risk of being exposed to sexually transmitted diseases, said male garment comprising:
    a bifurcated body formed from pliable and fluid-impermeable material and including integrally disposed front and rear sections, said body having a centrally disposed longitudinal axis and being removably positionable about a user's waist wherein said front section is oriented about a genital region and said rear section is oriented about a buttock region respectively, said front section being provided with a sheath sized and shaped for receiving a male penis therethrough, said sheath being integral with said front section and including a ribbed outer surface for maintaining a condom at a substantially stable position during love-making activities, said ribbed outer surface including a plurality of protrusions symmetrically spaced in multiple rows thereabout;
    means for fastening said garment about the user's waist so that said garment can be maintained at a substantially stable position during the activities; and
    a condom positionable about the penis wherein a proximal end portion of said condom is engageable about said ribbed outer surface of said sheath, said ribbed outer surface defining a frictional contact area for assisting to maintain said condom positioned about the penis during the activities;
    wherein said fastening means comprises
        a resiliently gathered elastic portion integrally attached to said rear section and being formed from elastic material for providing resilient tension about the user's waist, said elastic portion terminating at said front section such that said front section is freely adaptable during thrusting motions and unhindered by said elastic portion, and
        an additional gathered elastic portion attached to said rear section and providing resilient tension about a buttock region, said additional gathered elastic portion being spaced from said front portion, said additional gathered elastic portion having a longitudinal length that is shorter than a longitudinal length of said elastic portion;
    wherein said additional gathered elastic portion spans along a partial width of said rear section and is centered between left and right sides of said garment, said additional gathered elastic portion having a concentrated central elastic section that is substantially rectangular and spans substantially parallel to a waist of the user;
    wherein said fastening means further comprises: a plurality of resilient elastic sections extending along entire longitudinal lengths of respective longitudinal sides of said central elastic section respectively, wherein each of said resilient elastic sections has a corresponding elasticity that is less concentrated than an elasticity of said central elastic section.

2. The male garment of claim 1, further comprising: a plurality of pockets attached to said rear section of said garment for housing lubrication and said condom respectively.

3. The male garment of claim 2, further comprising: a plurality of elastic bands extending along lower most edges of said garment, each of said elastic bands extending along an entire perimeter of said lower most edges of said front and rear sections and thereby forming a continuous elastic perimeter around entire leg portions of said garment formed at said lower most edges of said garment.

4. A male garment for reducing the risk of being exposed to sexually transmitted diseases, said male garment comprising:
    a bifurcated body formed from pliable and fluid-impermeable material and including integrally disposed front and rear sections, said body having a centrally disposed longitudinal axis and being removably positionable about a user's waist wherein said front section is oriented about a genital region and said rear section is oriented about a buttock region respectively, said front section being provided with a sheath sized and shaped for receiving a male penis therethrough, said sheath being integral with said front section and including a ribbed outer surface for maintaining a condom at a substantially stable position during love-making activities, said ribbed outer surface including a plurality of protrusions symmetrically spaced in multiple rows thereabout;
    means for fastening said garment about the user's waist so that said garment can be maintained at a substantially stable position during the activities; and
    a condom positionable about the penis wherein a proximal end portion of said condom is engageable about said ribbed outer surface of said sheath, said ribbed outer surface defining a frictional contact area for assisting to maintain said condom positioned about the penis during the activities;
    wherein said fastening means comprises
        a resiliently gathered elastic portion integrally attached to said rear section and being formed from elastic material for providing resilient tension about the user's waist, said elastic portion terminating at said front section such that said front section is freely adaptable during thrusting motions and unhindered by said elastic portion, and
        an additional gathered elastic portion attached to said rear section and providing resilient tension about a buttock region, said additional gathered elastic portion being spaced from said front portion;
    wherein said additional gathered elastic portion spans along a partial width of said rear section and is centered between left and right sides of said garment, said additional gathered elastic portion having a concentrated central elastic section that is substantially rectangular and spans substantially parallel to a waist of the user;
    wherein said fastening means further comprises: a plurality of resilient elastic sections extending along entire longitudinal lengths of respective longitudinal sides of said central elastic section respectively, wherein each of said resilient elastic sections has a corresponding elasticity that is less concentrated than an elasticity of said central elastic section.

5. The male garment of claim 4, further comprising: a plurality of pockets attached to said rear section of said garment for housing lubrication and said condom respectively.

6. The male garment of claim 5, further comprising: a plurality of elastic bands extending along lower most edges of said garment, each of said elastic bands extending along an entire perimeter of said lower most edges of said front and rear sections and thereby forming a continuous elastic perimeter around entire leg portions of said garment formed at said lower most edges of said garment.

\* \* \* \* \*